(12) United States Patent
Selby

(10) Patent No.: US 11,237,088 B2
(45) Date of Patent: Feb. 1, 2022

(54) LUBRICANT TEST METHOD AND APPARATUS

(71) Applicant: Theodore W. Selby, Midland, MI (US)

(72) Inventor: Theodore W. Selby, Midland, MI (US)

(73) Assignee: Theodore W. Selby, Midland, MI (US)

( * ) Notice: Subject to any disclaimer, the term of this patent is extended or adjusted under 35 U.S.C. 154(b) by 0 days.

(21) Appl. No.: 17/300,003

(22) Filed: Feb. 1, 2021

(65) Prior Publication Data

US 2021/0239588 A1    Aug. 5, 2021

Related U.S. Application Data

(60) Provisional application No. 62/995,523, filed on Jan. 31, 2020.

(51) Int. Cl.
*G01N 11/14* (2006.01)
*G01N 33/28* (2006.01)

(52) U.S. Cl.
CPC ....... *G01N 11/142* (2013.01); *G01N 33/2888* (2013.01)

(58) Field of Classification Search
CPC ...... G01N 19/02; G01N 33/2888; G01N 3/56; G01N 33/30; G01N 3/565; G01N 11/14; G01N 11/16; G01N 11/162; G01N 11/10; G01N 11/165
USPC .............................................. 73/9, 10, 53.05
See application file for complete search history.

(56) References Cited

U.S. PATENT DOCUMENTS

| | | | |
|---|---|---|---|
| 2,067,996 A * | 1/1937 | Werder | G01N 33/30 73/10 |
| 3,190,109 A * | 6/1965 | Faville | G01N 33/30 73/1.89 |
| 5,388,442 A * | 2/1995 | Kumar | G01N 19/02 73/10 |
| 5,955,655 A * | 9/1999 | Evans | G01N 33/30 73/7 |
| 7,426,855 B2 * | 9/2008 | Aubele | G01N 19/04 73/150 A |
| 7,698,929 B2 * | 4/2010 | Wollenberg | G01N 33/2888 73/53.05 |
| 7,752,883 B2 * | 7/2010 | Mazuyer | G01N 19/02 73/9 |
| 8,149,004 B2 | 4/2012 | Raju et al. | |
| 10,302,619 B2 | 5/2019 | Evans et al. | |

(Continued)

OTHER PUBLICATIONS

Selby, U.S. Appl. No. 62/995,523 entitled, "Lubricity Determination," filed Jan. 31, 2020 A.D.

(Continued)

*Primary Examiner* — David A. Rogers

(74) *Attorney, Agent, or Firm* — Christopher John Rudy

(57) ABSTRACT

Lubricity of a sample of lubricant may be determined by precisely measuring temperature from friction generated between two or more moving parts in contact under force. For example, to carry this out, a rotatable pin and vee block test apparatus set forth in ASTM D2760-95 (Reapproved 2010) can be provided, and modified to provide its rotating pin with a hole longitudinally along an axis of the pin about which the pin rotates during testing. The hole is configured to receive, and for the testing receives, a thermocouple to measure temperature during the testing.

11 Claims, 6 Drawing Sheets

(56) References Cited

U.S. PATENT DOCUMENTS

| | | | | |
|---|---|---|---|---|
| 2013/0333790 A1* | 12/2013 | Pinel | .................... | C09D 175/02 |
| | | | | 138/145 |
| 2015/0068273 A1* | 3/2015 | Wolf | ...................... | G01N 11/14 |
| | | | | 73/9 |
| 2018/0003692 A1* | 1/2018 | Evans | .................. | C10M 113/06 |

OTHER PUBLICATIONS

ASTM D2670-95 (Reapproved 2010), Standard Test Method for Measuring Wear Properties of Fluid Lubricants (Falex Pin and Vee Block Method), May 2010 A.D.

\* cited by examiner

1B — RATCHET WHEEL LOADER
LOAD GAGE
V-BLOCKS AND JOURNAL
OIL CUP
TORQUE GAGE

RATCHET WHEEL DETAIL

LUBRICITY ANALYSIS REPEATABILITY
OVERLAY OF RUNS 1 & 2 OF GROUP 2 BASE OIL

GROUP 2 BASE OIL WITH 5% ANTIWEAR ADDITIVE
USING LUBRICITY TEST AND 25-LB STEPS 1 - 5

LUBRICANT TEST METHOD AND APPARATUS

This claims domestic priority benefits under 35 USC 119(e) of U.S. provisional patent application No. 62/995,523 filed on Jan. 31, 2020 A.D.

FIELD AND PURVIEW OF THE INVENTION

This concerns testing of lubricants to determine lubricity from a temperature read out, from which more efficient lubricants and lubricant-bearing systems can be provided. As such, it concerns methodology as well as apparatus for such a determination. A lubricant of concern may be a liquid, for example, an oil, or a paste product, for example, a grease.

BACKGROUND TO THE INVENTION

By way of a historical and anthropological introduction, throughout man's history, devices have been made to improve his individual and collective human life. However, man has also always had to simultaneously face the factors of wear and friction of whatever devices he has created. Things such as sandpaper, brakes, tires, slip-resistant coatings and other materials, and so forth aside, these two factors have always been major impediments to the success of such mechanical improvements to his physical life on Earth, and now outer Space.

Consequently—virtually from the invention of the wheel forward—the development and practice of lubrication has been sought to reduce the combination of wear and friction and thus to extend and improve the useful life of his devices. Considering how dependent today's civilization is on the virtual infinitude of such mechanical devices from wristwatches to huge motors, it is no surprise that society is so dependent on the control of wear and friction with inventively developed forms of lubricants and lubrication. With the passage of time and the accelerating development of mechanical devices, the need to understand and control the causes of friction and wear has grown intensively. Lubrication and its associated lubricants have become an area of growth in knowledge that is more basic to the support of modern life than is appreciated by most of those who depend on these lubricated devices.

Over the many years since the need for lubrication first arose (perhaps with the aforementioned development of the wheel), recognition of this need for offsetting destructive effects of friction and wear has been a basic factor in the applications of the mechanical devices, which have become more prevalent in human activities. Not surprisingly, as man has become more knowledgeable and adept in countering wear—either by simple replacement of parts, or by better techniques of lubrication—users dependent on these devices have become more dependent on those knowledgeable concerning such lubrication.

The use of lubricants in the reduction of wear and friction has a familiar positive term associated with it, called "lubricity." This positive lubricant-related word is occasionally used as a non-specific observation related to the ease of sliding one surface over another. Note, Raju et al., U.S. Pat. No. 8,149,004 B2, for example, in column 8, et cetera.

Of course, various devices have been invented and modified to assist in lubricant testing. Among these are the Falex pin and vee block test machines employed in ASTM D2760-95 (Reapproved 2010) methodology for the wear-reduction properties of lubricants such as formulated oils. Regarding greases, note Evans et al., U.S. Pat. No. 10,302,619 B2, which discloses grease wear resistance, which includes a device improvement for the testing of wear resistance of grease, or another organic paste product, to include a grease wear test device for testing the wear resistance of a grease or another organic paste product, which includes a "grease sleeve" such as depicted in FIGS. 2-4C. See also, U.S. Pat. No. 8,149,004 B2 to Raju et al.

GENESIS OF THE INVENTION

The lifetime of operation and dependability of mechanical devices having parts moving in forceful contact with one another are, to a lesser or greater degree, dependent on the interrelationship and information of two primary parameters, friction and wear, and the influence of another, which is the degree of lubricity provided by a lubricant—if and when used. Testing the effect of lubricants on friction and wear is the purpose of essentially all bench tests that have been designed for measuring abrasive friction and/or the amount of wear that occurs during such a bench test.

Among factors affecting lubricity is one that has received only cursory attention, namely, the temperature identifying the heat produced by abrasive friction. The greater the abrasive friction, the higher the heat generated at the surface at which such friction is occurring and the higher the temperature associated with that heat, if the heat's resultant temperature can be carefully collected and consistently measured. Thus, carefully measuring such temperature can be used as a comparative measure of the level of lubricity available from a lubricant.

It seemed reasonable that gathering relatively precise information on the temperature accompanying friction could offer a very effective way to understand even more information regarding the comparative benefits of lubricants. If collected carefully and continuously from contacting surfaces being abraded under pressure, for instance, such temperature measurement should provide basic information regarding friction and wear. This temperature, if measured with sufficient precision, should clearly and continuously give information reflecting the energy required to generate abrasive friction and its associated wear. For example, a friction/wear-producing instrument with the added capability of collecting meaningful and reproducible temperature information could provide precise information on the friction and wear process, when used to compare the lubricity of different lubricants for an application.

Thus, four interrelated parameters of friction, wear, temperature and lubricity may be more or less linked in the behavior of mechanical components in contact with one another, and this behavior has always presented challenges to the design, operation, and lubrication of mechanical devices. So, much effort has been expended to attempt to understand and improve the response of such devices and their lubricants through lubricant tests including those for evaluation and characterization of liquid and paste product lubricants such as oils and greases.

A technical elaboration with respect to the aforementioned four parameters, considered in view of wear, friction and lubricity, is set forth as follows:

Wear

"Wear" is a term commonly used to describe the non-catastrophic loss of some of the contacting surfaces of a device when those surfaces are under a degree of pressure or force while in motion. It is defined as progressive loss of some, usually comparatively small, amount of either or (usually) both of the surfaces in contact, depending on their composition and relative hardnesses. In virtually all circumstances in which wear occurs, it is considered a negative effect, negatively affecting the function of the apparatus or device in which it occurs. Such loss is a natural response to abrasion of all solid matter and its varied forms of occurrence has led to many solutions involving the choice of surface material as well as the interposition of liquid, particulate or gelatinous substances to slow the wear process. Such wear-reducing interposition is usually called lubrication and has been used by humans to preserve their devices since—it is said—the early use of food grease on wooden wheel-hubs.

The wear process is usually one in which the surfaces that are in pressured contact have very tiny pieces of one or both surfaces torn off by the irregularities of the opposing surface. With surfaces such as presented by some metals and the choice and degree of shaping and smoothing—small areas in sufficiently pressured contact may generate temperatures capable of melding or welding into larger masses, creating further and larger areas of irregularities. Depending on these various conditions and effects of abrading contact between two surfaces, such a wearing process can ultimately create significant damage and ultimate failure of that portion of the mechanical device. Moreover, the heat generated by such abrasive wear conditions may also generate another negative effect by the associated inordinately high temperatures rising in the immediate and surrounding area of the operating device.

Depending on the composition of the metal surfaces in contact and the physical and chemical composition of any lubricant applied, wear can be significantly modified but virtually never eliminated. Thus, among the problems faced by modern man is the reduction of wear of his incredible array of mechanical devices by the development, choice and application of lubricants and lubrication. This, in turn, directly depends upon his developing a keener understanding of the physics and chemistry of lubricity and, by this growth in understanding, further the durability and utility of man's multifarious devices.

Friction

A major impediment in virtually every mechanism developed by mankind is the resistance to the desired relative motion of two surfaces pressed together. Such resistance to relative motion has been termed "friction," and the process requires energy that could otherwise be used to advantage. Friction is a fundamental factor that must be taken into account in the design and use of virtually all mechanical equipment and devices. Moreover, friction also generates heat, and the related temperature increase must also be considered in mechanical design. Consequently, friction has been a very important consideration of equipment development and redesign as well as the formulation and use of lubricants over man's history.

As a companion of friction, wear most commonly varies from a tolerable role up to the point shortly before failure of the surfaces producing the friction, where it takes on a major role. However, while the use of lubricants has a major benefit in reducing both wear and friction, the viscous traction of lubricants also offers some resistance to motion even though it greatly reduces the energy lost in abrasion. Thus, for two major reasons, lubrication and lubricants have become major factors in mankind's existence today—particularly as modern life has become more and more filled with mechanical devices.

Lubricity

Considering the foregoing negative implications of wear and friction and the benefit given by proper choice of lubricants and lubrication strategies, it seemed of value to consider the mentioned positive aspect of lubrication called "lubricity," a term implying the relative ease of moving one surface over another when pressed together. Thus, it is a term virtually the opposite of the concept of friction and similarly varies from one kind of rubbing contact to another. Friction, however, can be defined in units of energy or work while lubricity has not been given technical measurement or dimensions. Considering the positive connotations of lubricity, it seemed desirable to develop further understanding and definition.

Accordingly, since reduction of friction and wear is clearly associated with improvement of lubricity, it was thought helpful to generate a lubricity test that would evaluate a lubricant by measuring the degree of reduction of the temperature generated by friction. Using a revolving pin having an associated thermocouple and vee blocks of selected metallurgy, a lubricant of interest would be compared to a reference base oil (or no lubricant at all) in the lubricity test. The ratio of the measured temperature of the latter (control) to that of the test lubricant under the lubricity test conditions imposed may be called the "lubricity index."

A further informative application of the lubricity test, and the lubricity index data generated from it, would be to develop and apply a bench test that stepwise, reproducibly applies several levels of force pressing vee blocks against revolving pins with thermocouples. For example, measurement of temperature by the lubricity test would provide information on the level of benefit of the lubricity of a given formulated oil at increasing levels of load. Thus, by comparing different lubricants under similar but increasingly strenuous analytical conditions, the effects of load on abrasion would be shown. That is, the less is the increase of frictional temperature, the better is the lubricity shown by the sequence of lubricity tests.

SOME DESIDERATA

It has always been sought, and yet is desirable here to improve the art and a useful and practical understanding of it. More particularly, among other desiderata, it would be desirable to understand more clearly the cause of wear and friction so that reduction of these two physical properties can be achieved. It would be desirable to more precisely evaluate lubricants and more pointedly employ the same as lubrication in order to reduce the friction and wear and further extend the useful life of many of man's mechanical devices. It would be desirable to assess friction, wear and lubricity in relation to the motion and materials of mechanical components in very near or actual contact with one another so that designing, operating, and lubricating mechanical devices having such mechanical components can be carried out more efficiently. It would be especially desirable to provide quantifications of lubricity and the measurement of the lubrication properties of a lubricant, for example, grease or another organic paste product, so that such designing, operating and lubricating as aforesaid can be more efficiently quantatively and qualitatively improved. It would be desirable, too, to precisely employ temperature as from friction to assess lubricity. As well, it would be desirable to provide the art with new apparatus for testing oil or another liquid lubricant to readily obtain a lubricity value. Further desiderata are extant in the art, to include as identified above and below, and are desirably improved.

A SUMMARY OF THE INVENTION

Provided hereby is an example of a particular method for obtaining precise temperature data for measuring lubricity of a sample of a lubricant, which comprises carrying out the following steps (A-G), which are not required to be carried out in series unless otherwise indicated:

A. providing a test apparatus having at least parts that move abrasively in relation to each other, each part having a surface able to be moved in abrasive contact under force with at least one other;

B. providing a baseline set of lubrication conditions between the surfaces in said contact with one another through addition of a baseline lubricant sample or avoiding employment of an added lubricant between said surfaces in said contact with at least one other;

C. abrasively moving at least one of said parts and applying force during that abrasive movement such that the abrasively moving forceful contact is carried out between said surfaces under said baseline set of lubrication conditions;

D. measuring temperature indicative of heat generated during said abrasive movement in abrasive contact under said baseline set of lubrication conditions;

E. repeating steps A-C, but replacing at least the surfaces of said abrasively movable parts with corresponding, fresh surfaces able to be moved in abrasive contact under force with at least one other, and replacing the baseline set of lubrication conditions with a target set of lubrication conditions through employment of a target lubricant between said surfaces;

F. measuring temperature generated that is indicative of heat generated during said abrasive movement in abrasive contact under said target set of lubrication conditions; and G. comparing the temperatures generated under the baseline and target set of lubrication conditions to generate a lubricity index of the target lubricant sample.

For example, the test apparatus can be a Falex pin and vee block test apparatus for ASTM D2760-95 (Reapproved 2010) testing, which advantageously is a modified pin and vee block test apparatus with its rotating journal (pin) having a central axis with a hole longitudinally along the central axis of the pin about which the pin rotates during testing. This hole is configured to receive a thermocouple to precisely measure the temperature of the accumulated heat generated during the testing. Also provided is an apparatus for obtaining a lubricity value of a liquid lubricant comprising a rotating pin and vee block test apparatus as otherwise set forth in said ASTM, but modified to have the hole longitudinally along the axis of the rotating pin, said hole configured to receive the thermocouple, which is adapted to measure temperature during testing, but without a "grease sleeve." The thermocouple can be received in said hole.

The invention is useful in lubricant testing. More particularly, as an operative or underlying theme, it relates to the use of precisely gathered temperature to determine the heat output of frictional abrasion of two surfaces as a measure of lubricity.

By the invention, the art of lubrication is improved in kind. One or more of the aforementioned desiderata is or are satisfied. Notably, a value for lubricity can be established for a lubricant in relation to materials of the pin and vee employed in the pin and vee block test apparatus, which can be used to practical advantage in order to provide more full and competent test results, and in the design, operation, and lubrication of mechanical components in very near or actual contact with one another in mechanical devices. Moreover, the present apparatus constitutes a breakthrough in liquid lubricant testing in that, although it appears simple in concept and structure, it significantly extends and surpasses the utility of the unmodified Falex pin and vee block test machine employed in ASTM D2760 testing of liquid lubricants such as oils, since now, with the present apparatus, a value for lubricity can be readily established for a liquid lubricant in relation to materials of the rotating pin and vee blocks employed in the apparatus. Lubricity indices may be comparably established for grease or other paste product lubricants through employment of the apparatus in Evans et al., U.S. Pat. No. 10,302,619 B2, and so forth. This value can be used to practical advantage in the design, operation, and lubrication of mechanical components in very near or actual contact with one another in mechanical devices. Numerous further advantages and testing devices utilizing the principle of precisely gathering the temperature produced by abrasion attend the invention.

DRAWINGS IN BRIEF

The drawings form part of the specification hereof. With respect to the drawings, which are not necessarily drawn to scale, the following is briefly noted:

FIGS. 1A and 1B depict a prior art Falex Pin and Vee Block test machine such as employed in testing pursuant to ASTM D2760-95 (Reapproved 2010) methodology for wear properties of what are termed, "fluid lubricants," i.e., e.g., oils, with FIG. 1A a perspective view of the test machine and FIG. 1B a perspective view of ratchet wheel detail referenced in FIG. 1A by reference numeral 1B. The same compares with a picture taken from the full manufacturer's specification manual on the Falex Corporation website. In that test method, a sample pan is used to hold a 60-mL liquid test sample in place during testing, at a starting temperature of 75° F. (24° C.). No further temperature is noted.

Figure 1A:
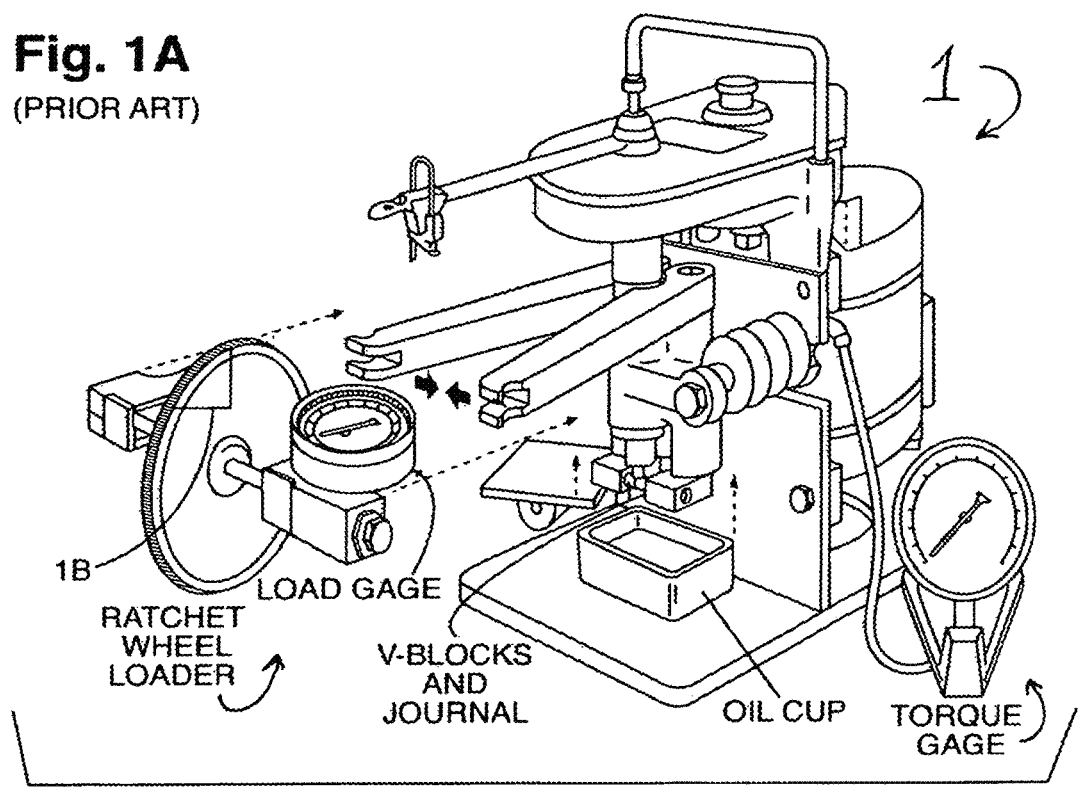

Within the drawings, among other things, may be found feature(s), part(s), subcombination(s) and/or combination(s) such as identified as follows:

| Reference Numeral | Identity |
|---|---|
| 1 | Pin and vee block test apparatus as set forth in ASTM D2760-95 (Reapproved 2010) |
| 2 | Rotating journal drive coupling |
| 3 | Brass locking/shear pin |
| 4 | Vee block |
| 10 | Rotating journal or pin |
| 11 | Hole for thermocouple |
| 12 | Thermocouple |
| 100 | Modified pin and vee block test apparatus of the invention for testing liquid lubricants, e.g., oils. |

ILLUSTRATIVE DETAIL

The invention can be further understood by the additional detail set forth below, which may be read in view of the drawings. The same, as in the case of foregoing, is to be taken in an illustrative but not necessarily limiting sense.

Provided is a method relating wear, friction and temperature, and lubricity. Lubricity is of particular interest as it relates to reasons for selecting a lubricant vel non for selection for employment in a machine having moving parts that come into contact with one another in order to reduce friction and/or wear. Provided also is an apparatus for obtaining a lubricity value, which may be a lubricity index, of a liquid lubricant, a grease or other paste product lubricant, and so forth and the like. It may be considered to be a modification of the test machine of ASTM D2760-95 (Reapproved 2010).

The sample of the lubricant for testing hereby may be made of any suitable substance. For instance, the lubricant may be an oleaginous liquid or paste product such as an oil or a grease; another liquid such as a lubricant composed of an organic compound or composition that is not considered oleaginous, a silicone lubricant, water, and so forth and the like. Whereas ASTM D2670-95 (Reapproved 2010) applies to testing oils, the modified apparatus as disclosed in U.S. Pat. No. 10,302,619 B2 is particularly suited for grease wear resistance testing. Employment of either or both of those testing methods and their apparatus, however, may be advantageously carried out for any suitable lubricant or lubricant candidate.

In view of the importance of lubricants in easing the negative aspects of wear and friction and improving the degree of lubricity, a modification of a dependable and long-used bench test known as the Pin and Vee Block Test as described in ASTM D2670-95 (Reapproved 2010) was made—the modification of interest in one aspect being the provision and employment of a revolving pin with a hole bored longitudinally along its rotational axis, with the hole configured to receive a thermocouple to measure temperature about the abrading surface of the rotating pin in the test oil sample and conducted through the pin through its center during the testing. This provides for measurement of heat in a contained system, an important factor in the precision of the testing. Of note, in the testing of grease or other paste product, which may be organic, the modification may go further to include a grease wear test device, also termed a grease sleeve or grease holder, plus the revolving pin having a hole longitudinally along the axis of it about which it rotates during testing, with the hole loosely containing the inserted thermocouple to measure temperature during the testing, as disclosed in U.S. Pat. No. 10,302,619 B2.

The technique developed and applied hereby takes advantage of the amount of heat generated by the friction of two metal surfaces pressing against one another in relative motion. As friction increases, the temperature of the contacting solid materials increases and lubricity decreases. In the case of metal and many if not all other surfaces most of the heat is conducted away in the normal pattern of trying to bring the pieces in contact, which may further take into account any surrounding gas, fluid or lubricant, to temperature equilibrium.

The temperature may be obtained in any suitable manner. Thus, it may be obtained from a direct measure of heat as by a thermocouple, from a remotely obtained measure of heat as by an infrared thermometer, or from any other suitable device or system.

In the special modification employed herein, a centered hole is provided, for example, by boring, in the bottom of a revolving pin extending beyond the area of contact between the pin and two opposing vee blocks pressed under measured pressure against the pin. A temperature-recording thermocouple is inserted up into the bore-hole in the pin during whatever form of pin and vee block bench test is chosen. The modification can be incorporated into a Falex pin and vee block device such as otherwise used in ASTM D2670-95 (Reapproved 2010). See also, U.S. Pat. No. 10,302,619 B2.

The pin-centered thermocouple at the center of the friction-heated pin reflects the degree of friction being generated under a given pressure imposed on the two vee blocks against the pin. Accordingly, a relationship is developed with respect to, if not inversely that of, or even mathematically reciprocal to, friction, based on this measured temperature, which can be viewed as related to the lubricity experienced at the rubbing surfaces. Coefficient constants can be determined for various materials of the pin and vee blocks and pressures applied during testing. Further, by imposing the same test conditions on different lubricants it is reasonable to compare their effectiveness in imparting lubricity.

Beneficially, the temperature is a precise measure of heat generated within the system.

Another important effect of wear is the energy that goes into causing it. This energy is some part of the usually much greater energy forcing the two surfaces sliding past one another under contact under pressure or force. Resistance to such motion has been termed "friction," or at least may be related to it, and is a fundamental factor in the design and use of mechanical equipment. It has been on of the most important causes of equipment development and redesign and redevelopment. Inspection of the wear surfaces of the pin and vee blocks employed in the testing can help in the design of mechanical equipment and selection of lubricant. As well, values for the friction encountered, and hence lubricity, can help determine more accurately how much wear is actually occurring beyond that which is presented by visual inspection.

The journal, which rotates during testing and again may be termed a "pin" or "Falex pin," and vee blocks may be made of any suitable material(s). Thus, the pin and vee blocks may be made of the same or different material(s). And so, the pin and vee block wear couple may be composed of the same or a plurality of different metal(s), metal alloy(s) and/or metal(s) and/or alloy(s) having the same composition but treated differently to afford different properties, for example, as may be afforded through heat treatment. As well, two vee blocks may be made of the same or differing materials. Other material(s) that may be employed as material(s) for the pin and vee blocks may be made of other metal(s) or metal alloy(s) of interest as they may present themselves as moving parts in various examples of machinery, for example, metal(s) such as, independently at each occurrence, beryllium, magnesium, titanium, vanadium, chromium, manganese, iron, cobalt, nickel, copper, zinc, zirconium, molybdenum, palladium, silver, cadmium, lanthanum, tungsten, platinum, gold, lead, actinium, and so forth and the like, and/or alloy(s) thereof. In lieu of or in addition to metal(s) and/or alloy(s) and so forth, the pin and vee blocks may be made of ceramic(s), mineral(s), diamond, plastic resin(s), high-tech composite(s), wood(s), and so forth. Mixing and matching of lubricant(s) with pin and vee blocks of differing composition or physical properties as part of the test couple can be employed. This can help determine which lubricant is more suitable for employment with which solid material(s) as contacting or rubbing couples in moving machinery.

Any suitable size Falex pin modified with any suitable size hole may be employed. For example, the modified Falex pin with a hole for a thermocouple may be made of steel, say, AISI 3135 steel, HRB 87-91 on a ground flat surface, surface finish 5-10 micro inches, rms, and be 1¼ inches long with a ¼-inch diameter. The vee blocks would correspond accordingly. For example, they may be standard coined vee blocks having a 96°+1° angle, made of AISI C-1137 steel HRC 20-24, surface finish 5-10 micro inches, rms. In the special modification hereof, the centered hole of the revolving pin can be a through hole, for example, provided by boring through a Falex pin along its central axis, or a blind hole, for example, provided by boring into the bottom of a Falex pin extending beyond the area of contact between the revolving pin and the two opposing vee blocks that are pressed under measured pressure against the pin. A through hole can provide more consistent results than a blind hole. The hole, however, accommodates insertion of the sensing end of a thermocouple. The thermocouple remains inserted into the bore-hole in the pin during whatever form of pin and vee block bench test is chosen.

Any suitable thermocouple may be employed. The thermocouple, however, should loosely fit in the hole.

The ASTM D2670-95 (Reapproved 2010) procedure but using the present apparatus may be carried out. Thus, motor oil may be tested with a steel Falex pin modified with a hole and vee block set for fifteen minutes with a starting temperature of 75° F. (24° C.). Temperature measured by the thermocouple is monitored and may be recorded. Such a procedure may be modified. A pin may be rotated at any suitable speed. For instance, it may be about from fifty or one hundred to two hundred or five hundred RPM. For example, it may rotate at the ASTM standard two hundred ninety RPM.

The technique developed and applied with the present apparatus takes advantage of the amount of heat generated by the friction of two metal surfaces pressing against one another in relative motion. As friction increases, the temperature of the contacting solid materials increases and lubricity decreases. In the case of metal and many if not all other surfaces most of the heat is conducted away in the normal pattern of trying to bring the pieces in contact, which may further take into account any surrounding gas, fluid or lubricant, to temperature equilibrium. As noted elsewhere herein, as an indication of generated heat, the temperature is desirably measured with respect to heat in a system, for example, by a hole-modified, thermocouple-received rotating pin.

The pin-centered thermocouple at the center of the friction-heated pin reflects the degree of friction being generated under a given pressure imposed on the two vee blocks against the pin. Accordingly, a relationship can be developed with respect to, if not an inverse to or even other function of that of, or even mathematically reciprocal to, friction, based on this measured temperature, which can be viewed as related to the lubricity experienced at the rubbing surfaces. Coefficient constants can be determined for various materials of the pin and vee blocks and pressures applied during testing.

Further, by imposing the same test conditions on different lubricants it is reasonable to compare their effectiveness in imparting lubricity.

Determining Temperature and Wear Related to Lubricity

Choice of Instrumentation

To repeatably measure the friction aspect of lubricity, a simple geometry of abrading surfaces was employed, which lends itself to repeatably generating the heat of abrasion and measuring its emanating temperature effects. The test for lubricity employed not only this simple geometry of abrading friction and wear surfaces but also an equally simple means of collecting the temperature output produced by the heat generated.

Figure 1B:
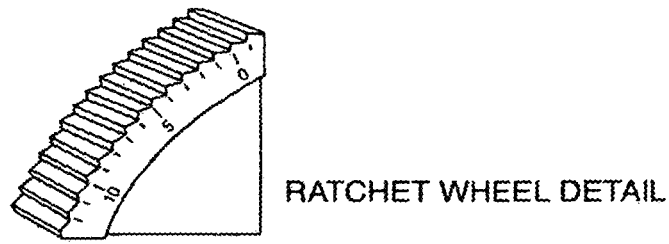
Figure 2:
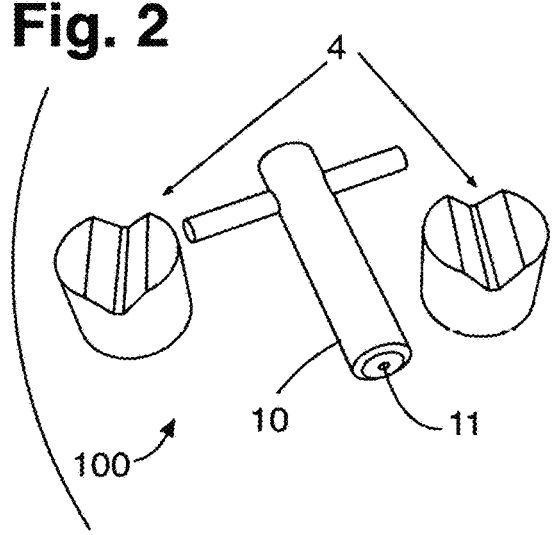
FIG. 2 is a perspective view of a rotating pin having a hole for receipt of a thermocouple longitudinally along an axis of the pin about which the pin rotates during testing. A pair of vee blocks are also depicted.
Figure 3:
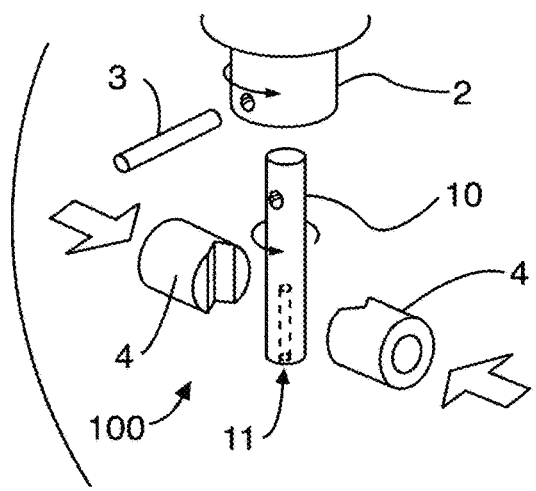
FIG. 3 is an exploded view of the rotating pin, thermocouple, and vee blocks of FIG. 2, for otherwise standard attachment to a falex pin and vee block test machine of FIGS. 1A and 1B.
Figure 4:
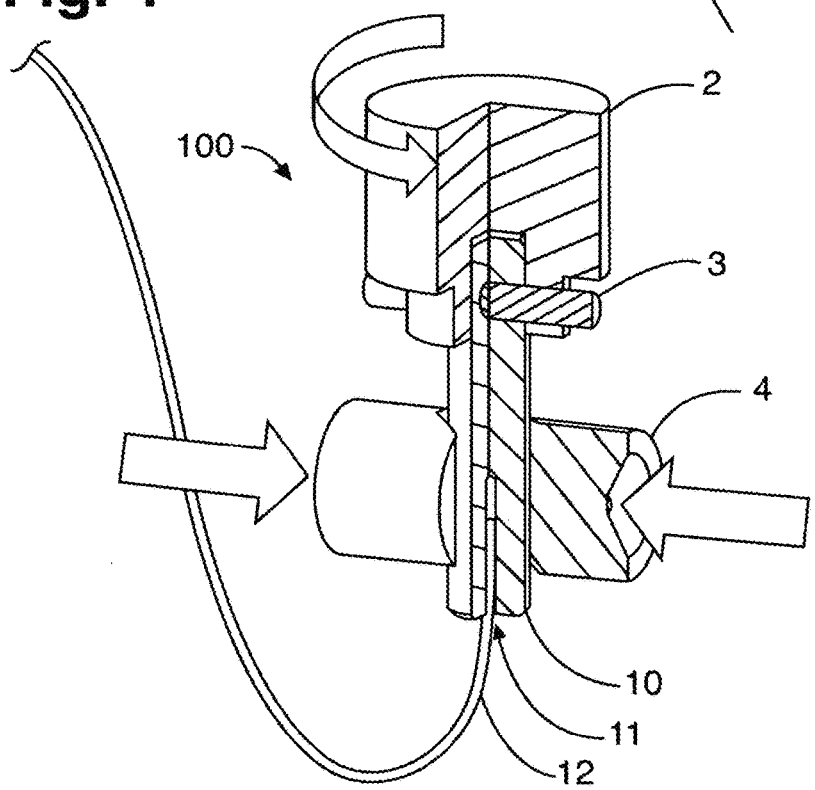
FIG. 4 is a sectional view of a portion of an assembled liquid lubricant test apparatus hereof, which can be incorporated into a falex pin and vee block test machine such as depicted in FIGS. 1A and 1B to modify the same to provide an embodiment of the assembled liquid lubricant test apparatus hereof.

Chosen was an instrument used in a bench test known as the pin and vee block (P/V) test (ASTM Test Method D2670) as depicted in FIGS. 1A and 1B. It had the desired important design feature of a centered pin rotor on which cylindrical surface all of the friction and wear during test was reliably and reasonably repeatably generated. By careful modification of the original rotor as shown in FIGS. 2-4 into which a selectively sized and centered passage was made for inserting the sensitive tip of a selected thermocouple.

As also shown, as with standard Falex pins, the modified Falex pins are pincered under load between two shaped vee blocks. But, whereas the original rotors only gave a measure of surface wear at the conclusion of test, the present rotating pin not only is continuously responsive to the temperature produced by friction on the pin—and thus, a measure of lubricity—but also is responsive to the resistance generated by wear and friction during test by measuring torque.

Lubricity Tests

A friction and wear test was then employed to determine lubricity as related to the temperature produced by the heat of friction and wear using the present, modified Falex pin in the P/V instrument. The first set of tests were carried out to appraise and compare response of the contacting metal surfaces of the rotating pins and vee blocks as influenced by the presence of a mineral oil alone, followed by tests with the same mineral oil modified by a commercial antiwear additive. Repeating these tests also gave a view of the precision of this new analytical technique.

The mineral oil used was a commercial Group 2 base stock of 5.08 cP viscosity at 100° C. Data using this base oil was followed by examinations of the base oil having 5% by weight of a commercial antiwear additive containing 0.2% by weight molybdenum disulfide ($MoS_2$), which gave it a slightly higher viscosity of 5.19 cP at 100° C.

Heat-Related Friction and Wear of Base Oil

The following was carried out:

Setup of Lubricity Test

This test setup used 60 mL of test fluid starting at an ambient temperature of about 25±5° C. A 290-RPM journal rotational speed was used during testing. As an added step to help repeatability, surfaces of the vee blocks and Falex pin that would come in contact during test were gently rubbed by ten light strokes with a cloth wet with a fluid containing a very fine abrasive to remove any tiny metallic excrescences left from their manufacture. This helped provide more closely equivalent surfaces for testing. Of course, this rubbing fluid was carefully removed from the vee blocks and rotating journals before testing commenced.

Measurement of Wear

One of the benefits of modifying the P/V instrument concerned measuring wear during testing. Wear is indicated by decrease in diametrical distance between the two vee blocks pincering the pin. Such change can be fairly closely and reproducibly approximated by counting the number of ratchet-wheel gear-teeth that are necessary to be advanced to close the diametrical distance after wear has occurred during and after a test period. Thus, during a test for lubricity of a lubricant, wear is measured periodically by the number of ratchet-wheel gear-teeth advanced as vee block pressure is increased on the modified Falex pin. On the P/V instrument used, each tooth advanced was determined to be equivalent to a 0.0694 thou (thousandth of an inch) closure of the vee blocks on the rotating journal. Compression of the steel under the imposed load would be a very minor and repeatable part of any change in diametrical distance caused by wear.

Running the Lubricity Test

After having set up the test components and immersing the assembled vee blocks and modified pin containing the thermocouple tip into the test fluid to the proper depth, an initial break-in is ready to be run. A 10-pound load, or somewhat less, is placed on the vee blocks pincering the modified pin, and the motor turning the pin is started and will not be turned off again until the test is completed. Load on the vee blocks is brought to a 100-pound value, and the break-in of the journal and vee blocks is conducted over a break-in period of 5±0.2 minutes.

Immediately after the break-in is completed, the load on the vee blocks is increased to a 125-pound value, and a ratchet-wheel gear-tooth is marked to establish its position as setting the zero point for subsequent measures of wear by the count of ratchet-teeth. This 125-pound load setting of Step 1 of the test for lubricity is maintained for 15±0.1 minutes. The load is then advanced to a 150-pound value for Step 2, and the ratchet-wheel gear-teeth are read immediately to determine the wear that has occurred in Step 1. Progressive steps include a 25-pound load increase and determination of wear in the previous step, until failure when the combined friction and wear resistance become great enough to cause severance of the brass shear pin shown in FIGS. 2-4 that affixes the rotating journal within the P/V instrument's drive coupling.

Analysis of Base Oil

As mentioned above, for comparison, the test for lubricity was applied to a commercial Group 2 base oil, and test results were collected as a plot of both 1) torque resistance given by the friction and wear generated at the two vee block contact areas on the modified rotating journal, and 2) temperature recorded by the thermocouple within the modified rotating journal.

Results from First Base Oil Test

After the recording sensors for torque and temperature were turned on and assembly of the components competed, the test for lubricity of the base oil was initiated by turning on the motor of the P/V instrument continuously for the entire test.

Figure 5:
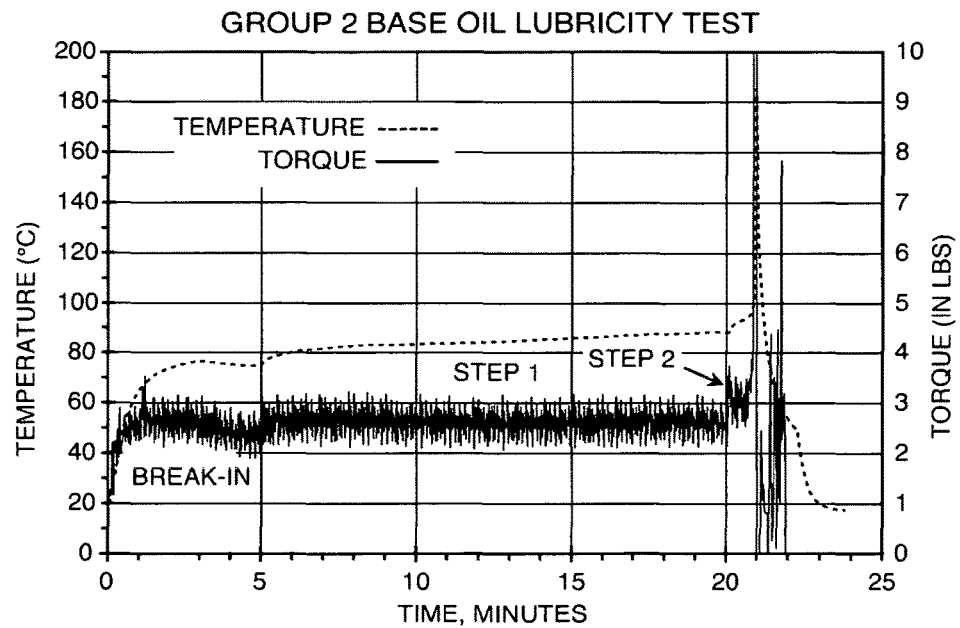
FIG. 5 is a graph of a lubricity test of a commercial Group 2 base oil to compare its performance in a test of the invention, with and without a commercial antiwear additive.

Shown in FIG. 5 are the friction and wear data obtained from the test for lubricity of the base oil. Inability of the base oil to provide lubricity sufficient to prevent failure was observed shortly (within a minute) after the 150-pound load in Step 2 was applied. Interestingly, the constant level of torque observed during Step 1 gave no indication of the limited lubricity range of the base oil as shown by its clear failure response to Step 2.

The previously noted reasons for developing the present test are supported by the level of agreement between the temperature and torque traces shown in FIG. 5, despite the oscillating nature of the torque trace. As would be expected, the temperature trace smoothly reflects the change of energy occurring as the friction changes between the vee blocks and the rotating journal. During the preliminary break-in, the temperature first rises and then mildly decays as the contacting components broaden their contacting surface areas by wear, which enhances whatever lubricity the base oil may be able to contribute. There is, however, an evident and interesting slowly rising temperature trace during Step 1.

Averaging the Torque Trace

Figure 6:
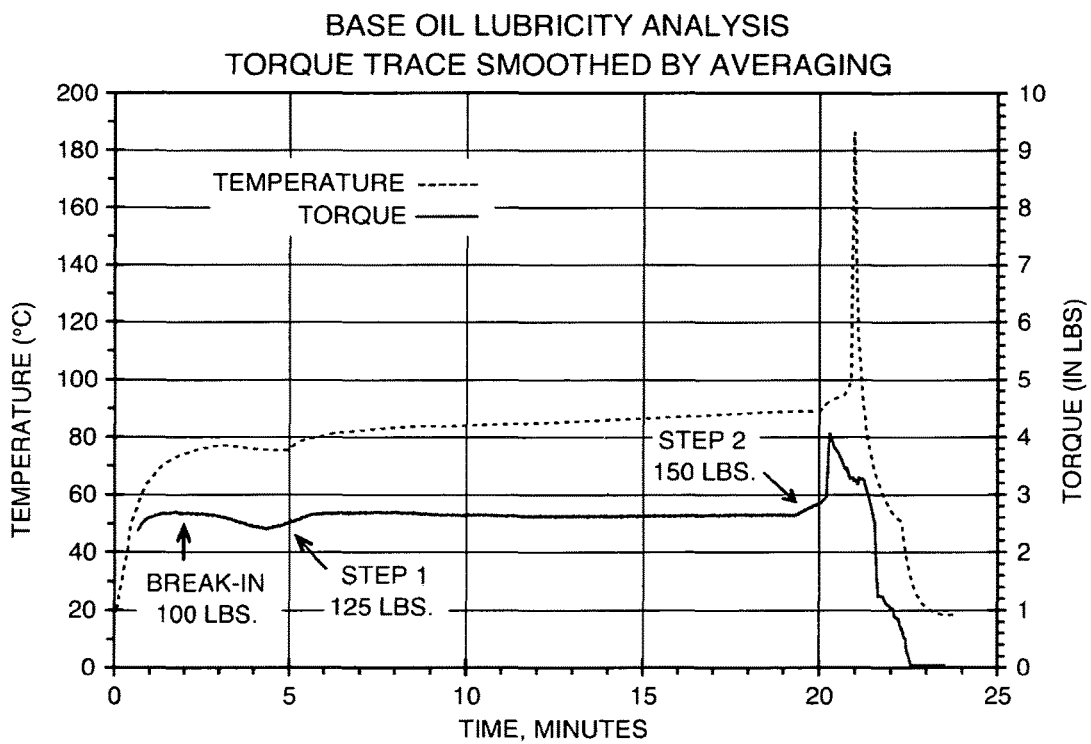
FIG. 6 is a graph of a torque trace in comparison to that found in FIG. 5.

To provide greater information from these torque traces and knowing that the true torque value was central within its oscillatory variation, it seemed best to improve the visual deficiency of torque in FIG. 5 by averaging the numeric torque data over a relatively small period of time. Consequently, each torque value, which the associated computer had taken progressively from the torque recorder each two seconds, was the average of approximately one minute of collected data. The benefit of this approach is shown in the FIG. 6 by comparing its torque trace with that of FIG. 5, as FIG. 6 is clearly more definitive and informative.

Analysis of Step 1 Data

After the break-in procedure at a 100-pound level, and without stopping the rotating modified journal, Step 1 is begun with a 25-pound load increase on the pincering vee blocks. Friction immediately increases, as shown in FIG. 6 by both temperature and torque traces. Again, this increase in load immediately establishes the zero reference ratchet-wheel, gear-tooth position for determination of the wear resulting from each of the 25-pound increases in load of subsequent steps.

With a 125-pound pincering load on the rotating journal at Step 1, the torque rises from 2.42 to 2.65 in.-lbs., and the temperature rises from 77° C. to 83° C. At that point, the torque becomes essentially constant at about 2.63±0.02 in.-lbs. The temperature slowly continues to increase at about 0.5° C. per minute over the 15-minute span of Step 1. This showed an interesting difference in measuring abrasive resistance by both torque and its expression of force necessary to overcome such resistance while the heat generated by the friction and wear requiring that force cannot be readily dissipated, which results in an increase in temperature.

Step 2 Data—Failure

Less than a minute after applying the second 25-pound load increase on the rotating, modified journal to initiate Step 2, the level of resistance to rotation owing to friction and wear became too strong. Consequently, the drive coupling (e.g., FIG. 4) cut the brass shear-pin used for the purpose of avoiding effects of such failure.

There was, however, enough time to determine the wear for Step 1 using the ratchet-wheel gear-teeth. Table 1, which is set forth below, shows the wear for Step 1 was 1.32 thou (thousandths of an inch). Interestingly, this wear was greater than that occurring during the break-in procedure.

Experimental Table 1

| Load (Lb.) | Teeth Initial | Teeth Final | Time (Min.) | Step No. | Wear (Thou Inch) Wear | Wear (Thou Inch) Total |
|---|---|---|---|---|---|---|
| 100 | 183 | 200 | 5 | 0 | 1.18 | zero |
| 125 | 200 | 219 | 15 | 1 | 1.32 | 1.32 |
| 150 | 219 | * | <1 | 2 | * | 1.32 |

*Run failed shortly after elevation to the 150-pound load.

This indicates that the amount of metal removed from both the journal and the vee blocks during break-in is not great, when wear is measured by diameter change.

Second Lubricity Test of the Base Oil

Considering the amount of information provided by FIG. 6 and Table 1 of the first analysis of the base oil, a second analysis of the base oil was made by another test for lubricity in order to to determine the repeatability of such information. The foregoing protocol and other steps were carried out.

Results of Second Base Oil Test

Figure 7:
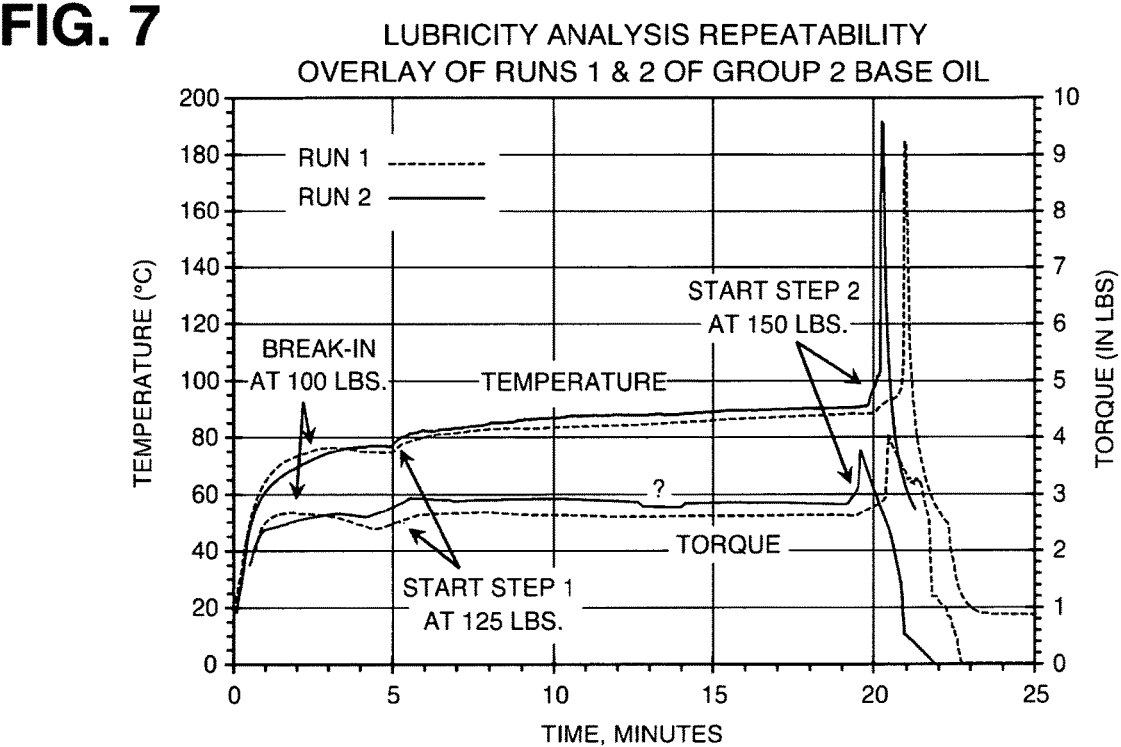
FIG. 7 is a co-plot of two lubricity tests showing good agreement for an abrasion and wear test of the same mineral oil.

The results of the second test for lubricity of the Group 2 base oil are shown in FIG. 7 and are co-plotted with the first test data shown in FIG. 6. Considering the complexity and extent of information provided by the first lubricity test, it is evident from FIG. 7 that the two tests show a good degree of repeatability in determining the response of a fluid having limited lubricity.

Failure at 150-Pound Load

Once again (and certainly not surprisingly), the base oil failed to provide sufficient lubricity to continue the test at the 150-pound load level. Moreover, failure occurred even more rapidly: approximately thirty seconds versus slightly less than one minute in the first test for lubricity of the base oil.

Wear

As shown in Table 2, which is set forth below, the break-in value of 1.25 thou for the second test for lubricity of the base oil is close to the value of 1.18 thou in Table 1 for the base oil's first test for lubricity.

Experimental Table 2

| Load (Lb.) | Teeth Initial | Teeth Final | Time (MM.) | Step No. | Wear (Thou Inch) Wear | Wear (Thou Inch) Total |
|---|---|---|---|---|---|---|
| 100 | 175 | 193 | 5 | 0 | 1.25 | zero |
| 125 | 193 | 217 | 15 | 1 | 1.67 | 1.67 |
| 150 | 219 | * | <1/2 | 2 | * | 1.67 |

*Run failed very shortly after elevation to the 150-pound load.

Failure here came even more quickly than in the first test, with barely enough time to determine wear. This more rapid failure may have resulted in the somewhat greater wear shown in Step 1 which was 1.67 thou, −0.35 thou greater than the 1.32 thou in the first test for lubricity of the base oil.

Also, with respect to the more rapid onset of failure and the increased level of wear shown in FIG. 7 and Table 2 found in the second lubricity test, after break-in and bringing the load on the rotating pin to a 125-pound value, FIG. 7 shows a small question mark on the torque trace from a relatively brief, slight and unusual 0.15 in.-lb. decrease in the torque trace at about 8-9 minutes. The cause of this sudden change is not known but its occurrence suggests a slight loss of friction between the vee blocks and the rotating pin, which might have influenced the more rapid failure.

Evaluation of Effect of a Commercial Antiwear Additive

On the basis of the performance of the base oil, the test for lubricity was applied to the base oil as enhanced by an antiwear-additive claiming beneficial results. Accordingly, 5% by weight of a commercial antiwear additive was blended with the base oil. Analysis of the finished blend showed that it contained approximately 0.05% of $MoS_2$—a compound which has been used in several additives over a number of years. The amount of this commercial additive put in the base oil reflected common levels recommended by additive experts.

Effects of Additive in Lubricity Test Procedure

This blend was then evaluated by applying the test for lubricity as above to observe the additive's effects on lubricity in comparison to that of the simple Group 2 base oil alone. Again, the break-in was at a 100-pound load for about five minutes, with the subsequent steps taken in 25-pound increases of load on the vee blocks pincering the modified rotating Falex pin.

Results of Lubricity Test

Results were obtained, as follows:

Observations from Initial Data

Figure 8:
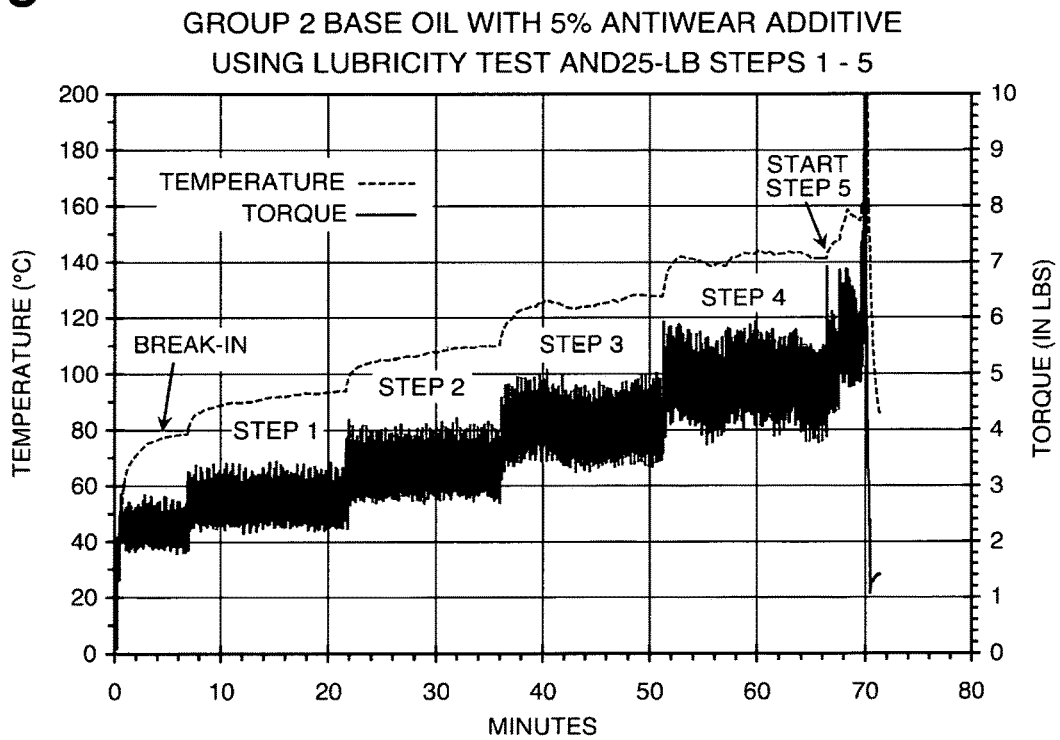
FIG. 8 is a graph of a lubricity test of base oil using 5% additive.

Unaveraged torque results of this test for lubricity are shown in FIG. 8.

An impressive change is shown by comparison of FIG. 5 with FIG. 8. It is evident that the addition of 5% of the antiwear additive has had a very significant, positive influence on the lubricity of the base oil. With the presence of the antiwear additive, the abrading surfaces of the vee blocks and rotating journal can tolerate a marked increase in load, namely, with the neat base oil, the failure reproducibly caused by increasing the 125-pound load to a 150-pound value does not occur until the load applied in 25-pound increments reaches a 225-pound value.

FIG. 8 also shows that the oscillation of the torque trace grows with increase in load. This would imply that the resistance to motion of the interfacing surfaces of the vee blocks to rotating journal increases with load. Also, the oscillation of the torque trace increases with higher load and friction, which may imply that the two interfacing surfaces are undergoing some further form of interaction.

Replot of Data Using Averaged Torque

The oscillatory torque trace in FIG. 8 is more difficult to understand than that found in FIG. 5. Accordingly, the torque information is averaged as previously described and applied for FIG. 6, and replotted and presented in FIG. 9. The clarification, moreover, is even better.

Figure 9:
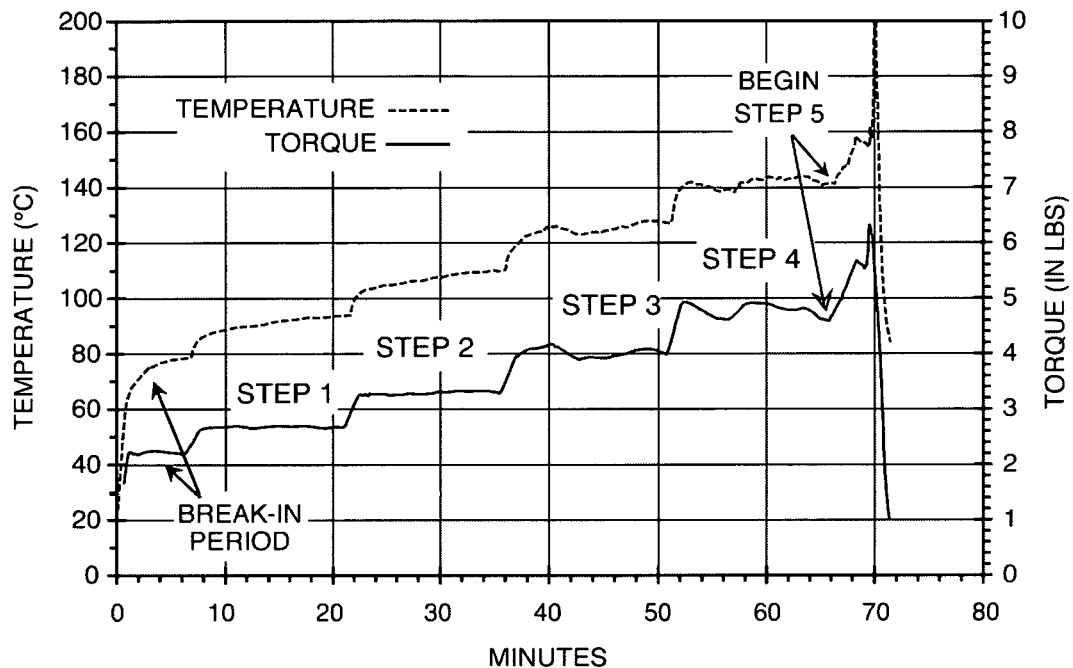
FIG. 9 is a graph of a lubricity test of a base oil with 5% additive using averaged torque.

Averaging the oscillatory torque data of FIG. 8 to produce FIG. 9 permits the torque data to show its close parallelism to that of the temperature and allows some interesting observations that could not be readily made otherwise. For example, lubricity test data of the torque-averaged FIG. 9 shows that the increased lubricity imparted by the addition of 5% of a commercial antiwear additive contributing 0.05% $MoS_2$ to the Group 2 base oil, increased the tolerable friction before failure from a torque of 2.7 in.-lbs to about 4.7 in.-lbs at the end of Step 4, a virtual doubling of resistance.

Also, the rising friction of the five increasing-load steps in this test substantially raises the temperature shown by the rotating journal from about 80° C. at the end of the break-in to approximately 143° C. at the end of Step 4.

Temperature and Torque

The increase in levels of the rotating pin temperature reflects the increase in torque accompanying each step of this test of the additive-modified base oil. In turn, both reflect the increasing levels of friction between the vee blocks and the rotating pin. It is of interest to compare the level of change of these critical properties, and this is shown below in Table 3.

Experimental Table 3

| Load (Lb.) | Step No. | Time (Min.) | Temperature (° C.) End of Step | Increase | Torque (in.-lb.) End of Step | Increase | Wear (Thou Inch) | Wear Total |
|---|---|---|---|---|---|---|---|---|
| 100 | 0 | 5 | 81.1 |  | 2.33 |  | 1.249 | 1.249 |
| 125 | 1 | 15 | 95.4 | 14.3 | 2.75 | 0.42 | 1.665 | 2.914 |
| 150 | 2 | 15 | 112.6 | 17.2 | 3.38 | 1.05 | 1.457 | 4.372 |
| 175 | 3 | 15 | 130.4 | 17.8 | 4.13 | 1.80 | 1.527 | 5.898 |
| 200 | 4 | 15 | 150.0 | 19.6 | 5.10 | 2.77 | 1.874 | 7.772 |
| 225 | 5 | 3 | * | * | * | * | * | * |

*Run failed three minutes after application of the 225-pound load.

The improved lubricity of the additive-containing base oil permits it to continue to permit the abrasion of the contacting surfaces of the journal and vee blocks through a load increase of about 60% even though friction shown by torque has increased by 85%. This increase in friction, in turn, increased the abrasive heating of the journal and raised its temperature from about 80° C. at the end of break-in to 150° C. at the end of Step 4. The capacity to increase the load to such an extent shows that the lubricity added by the antiwear additive to the lubricity of the base oil is substantial.

Onset of Apparently Slightly Varying Rubbing Contact

Another interesting aspect of the temperature and torque plots is also found in FIG. 9. First, during Steps 1 and 2, the plotted data are fairly smooth after adapting to the increase in friction caused by the increase in load. Expectedly, the journal temperature imitates both the torque increase and following smoothness, and again shows the gradual small increase over the remaining period of Steps 1 and 2, as observed and noted in the base oil's first step (FIG. 5). At Step 3, however, after imposing an additional 25-pound load, for approximately a minute the torque rises quickly from 3.38 in.-lb. to 4.00 in.-lb. in a manner similar to that which is found in Steps 1 and 2; then it rises more slowly for another three minutes to a torque of 4.16 in.-lbs.; after which it slowly decreases for three minutes to 3.90 in.-lbs.; and then it very slowly and slightly rises again to the end of Step 3.

The temperature plot fairly closely mirrors the torque plot, and thus shows that the rubbing contact goes through some change. The close imitation of torque by the temperature sensed by the thermocouple in the modified Falex pin journal is further evidence that the heat of abrasion directly influences the temperature of the thermocouple.

In Step 4, this slightly variable torque behavior increases, and the temperature continues to emulate the torque. The torque variation starts with an increase after which there is a decrease until another sequence of further torque increase/decrease. Such a pattern suggests a surface is formed and abraded away in the increasingly tight, lubricated contact of the vee blocks and journal. Finally, with Step 5—whatever the cause of the previous variable behavior of torque in Steps 3 and 4 may be—the increase in pressure becomes sufficient to cause failure.

Such evidence of variable behavior prior to failure may relate to the manner in which the abrading journal and vee blocks are affected by the antiwear additive in avoiding failure.

Wear

Figure 10:
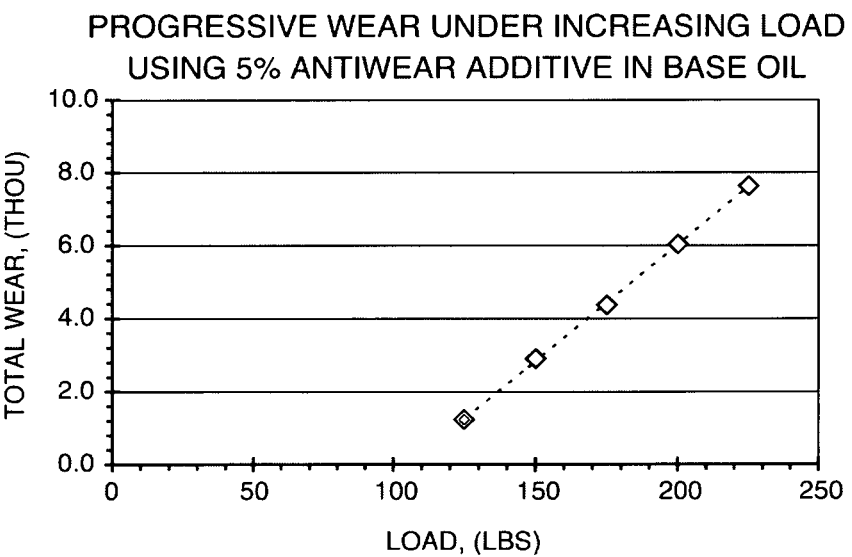
FIG. 10 is a graph of wear effects of increasing load.

One of the most important aspects of lubrication is in preventing wear. Comparing wear data obtained during progressive steps of a lubricity test is very informative as seen in FIG. 10, which depicts the total wear that has taken place at each step to include the initial loss during break-in which is shown by a slightly differently appearing point.

Interestingly, the data are very linear. That is, rather than the amount of wear increasing with increase in load, the amount of wear remains constant from step to step, with a high value of linear coefficient of determination ($R^2$=0.999).

Thus, whatever form of film of lubricant is being provided by the additized base oil and even though the pressure placed on the journal by the vee blocks is increased at each step, the wear rate is not changed. This may indicate an interaction of the antiwear additive with the contacting and abrading surfaces of the journal and vee blocks.

This information supports the antiwear claims that are associated with this and other molybdenum disulphide containing additives.

Second Analysis of Base Oil Plus 5% Antiwear Additive

Information produced by the first application of a lubricity test to the abrading surfaces of the modified Falex pin and vee block apparatus called for a second analysis like the first. But, considering the information produced by the first test of the additized base oil, even greater care was taken in preparing the contacting surfaces of the journal and vee blocks for the test.

Results

Figure 11:
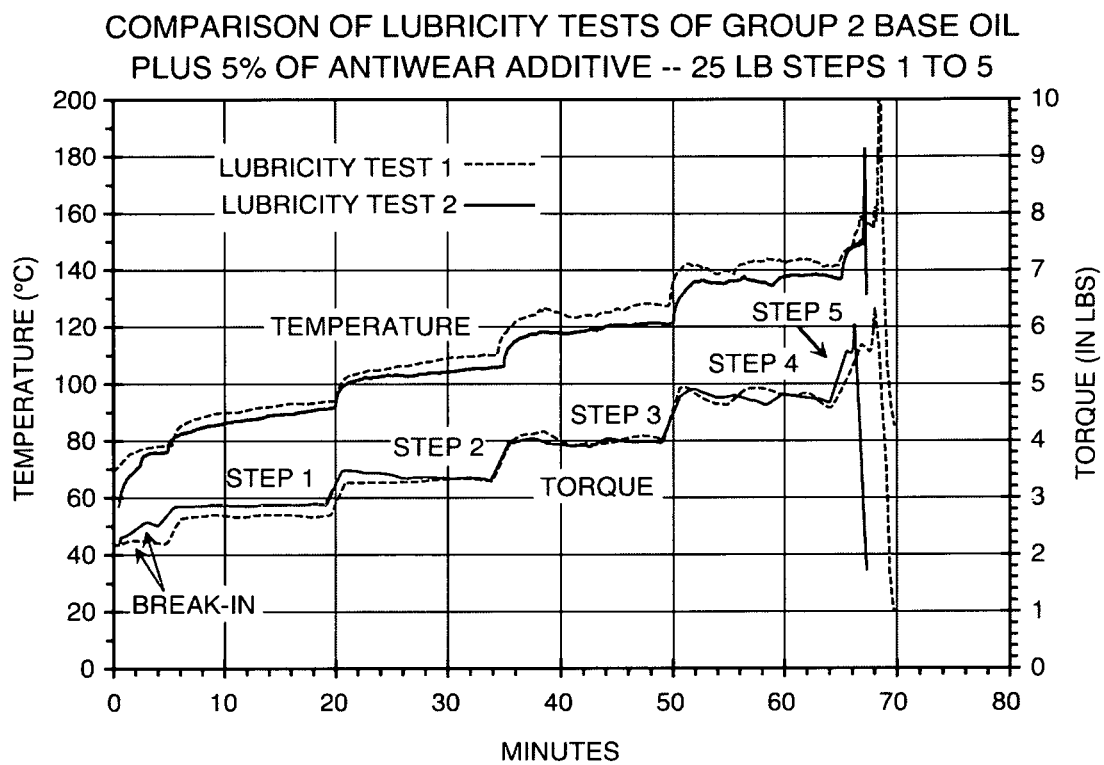
FIG. 11 is a comparison of two lubricity tests of the base oil containing 5% of an antioxidant additive.

Results of this second test are shown in FIG. 11, which may be compared with FIG. 9.

FIG. 11 shows that the torque and temperature traces of this second lubricity test on the antiwear-additive-containing base oil fall very close to those of the first test, and perhaps are somewhat smoother as a result of the additional care given the contacting surfaces in preparation. The failure load was identical at the 225-pound level, as was failure time after load application.

Observations

The similarity of the torque and temperature traces in FIG. 11 were noteworthy. This extended response of the lubricity test to the improved lubricity of the base oil with the antiwear additive did not cause loss of either sensitivity or reproducibility of the test. A good degree of reproducibility for a wear test is shown through all five steps of increasing load on the journal.

Torque Variation at Higher Loads

The degree of reproducibility was particularly evident regarding the torque variation in Step 3 and Step 4. In the first test for lubricity with the additive-containing base oil, it was noted that, in contrast to the relatively smooth plotted data of Steps 1 and 2, the torque data oscillated somewhat. It was of interest to see whether this pattern would repeat in the second test. As is evident in FIG. 11, the torque oscillation is definitely repeated giving greater support to the repeatability of the lubricity test and more reason to determine the cause of such oscillation at higher loads prior to failure.

Temperature and Torque

Table 4, which is set forth below and pertains to the second test for lubricity for the additized base oil, shows the values of torque and temperature recorded at the end of each of Steps 1, 2, 3 and 4, as well as their values at the end of the initial 5-minute break-in period.

Experimental Table 4

| Load (Lb.) | Step No. | Time (Min.) | Temperature (° C.) End of Step | Increase | Torque (in.-lb.) End of Step | Increase | Wear (Thou Inch) Wear Total |
|---|---|---|---|---|---|---|---|
| 100 | 0 | 5 | 77.9 | | 2.60 | | 1.180 1.180 |
| 125 | 1 | 15 | 92.7 | 14.8 | 3.01 | 0.41 | 1.527 2.706 |
| 150 | 2 | 15 | 108.0 | 15.3 | 3.43 | 0.42 | 1.735 4.441 |
| 175 | 3 | 15 | 123.5 | 15.5 | 4.08 | 0.65 | 1.735 6.176 |
| 200 | 4 | 15 | 139.3 | 17.1 | 4.79 | 0.71 | 1.249 7.425 |
| 225 | 5 | 2 | * | * | * | * | * * |

*Run failed two minutes after application of the 225-pound load.

Again, as previously shown in Table 3, the progressive increase in load on the journal also shows an increasing level of step-to-step change for both torque and temperature. A reasonable presumption is that increasing the load at each step would be expected to increase the level of friction and heat generation at the rubbing interface between the journal and the vee blocks. This is, in fact, the case, with considerable effect shown by torque.

Wear

Since wear is perhaps the most serious consequence of abrasive contact of two surfaces under load in a mechanism, one of the more important observations in the first lubricity test on the additized base oil was in regard to the surprising very linear rate of wear sequence shown in FIG. 10. That is, the wear rate did not increase with increased load but rather stayed essentially constant. Thus, it was important in this second test on the additized base oil to determine if this same wear sequence is produced and how this information compares to that of FIG. 10.

Figure 12:
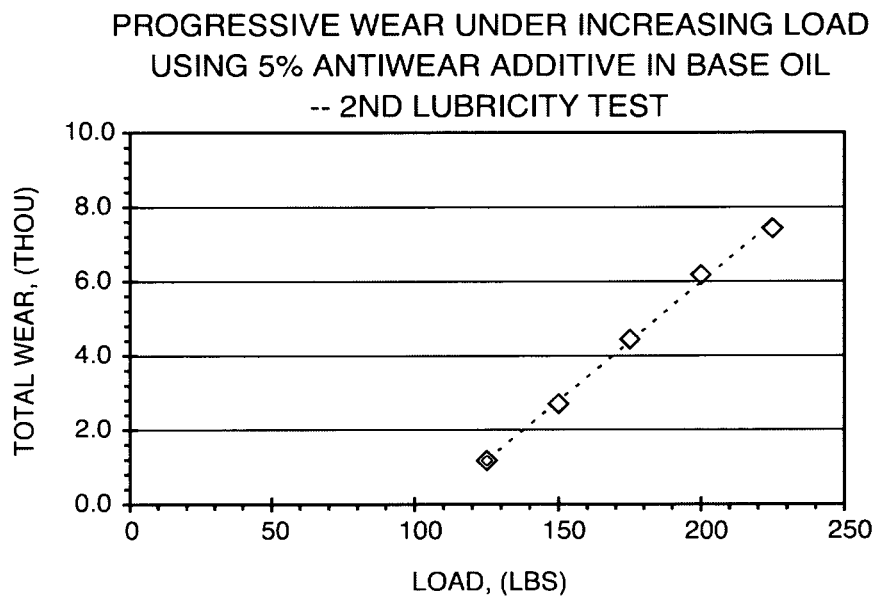
FIG. 12 is another graph of wear effects of increasing load.

FIG. 12 shows the same linear wear sequence previously seen in FIG. 10. Again, as evident in Table 4, the wear produced at each step of increasing load remains surprisingly constant despite the fact that the 25-pound step-wise increases in load placed on the modified rotating journal by the vee blocks have been ultimately changed from 100-pound to 200-pound values.

Moreover, the rate of wear of the two abrading surfaces of the journal and the vee blocks in the second test is very similar to the first. The data shown in FIG. 12 have a coefficient of determination of $R^2=0.998$.

Concluding Discussion

The following considerations are noted:

General Considerations

As has been observed frequently, over many years, mankind has had concerns about the resilience and service of his mechanical devices and mechanisms. Accordingly, he has engaged in many different studies of the cause of wear and failure. Understandably, these studies have primarily focused on the more obvious and detrimental aspects associated with both. While wear and failure are quite critical to the life of a mechanical device, technical studies of how to reduce their adverse effects have always been somewhat difficult because of reproducibility of developed tests. Nonetheless, much thoughtful and careful studies have been conceived and applied over man's technical dominion on this earth that have generally advanced his civilization.

The test technique and apparatus applied herein can measure progressive wear by a procedure otherwise employed in the ASTM D-2670 Pin and Vee Block Test Method.

The technique developed for measuring temperature generated by abrasion appears to be sensitive, informative and repeatable. Moreover, such temperature data is basic to the nature of the energy expended in opposing resistance to abrasive motion that is the heart of wear and friction. Interestingly, while increase in temperature is often thought directly related to an increase in friction and wear, some lubricants may cause contradiction to that assumption. And, even relatively near failure, increasing temperature may reflect increasing friction but not increasing wear.

The precise determination of the temperature of friction and wear as measured in the present test for lubricity provides a very useful measure of the comparative effectiveness of lubricants and additives to enhance lubricity and reduce such wear and friction.

More Specific Considerations

Employment of this precise technique of measuring the variation of temperature generated by the frictional energy produced in the progressive abrasion of two surfaces under systematically increasing rubbing pressure is highly beneficial. The more focused goal hereof, of course, was to find a sufficiently precise and informative method to compare the lubricity of various substances used as lubricants.

To do so required gathering the temperature generated by friction in a very simple and dependably reproducible manner. Placing a temperature-sensing thermocouple at the center of a cylindrical source of friction was advantageously employed. As has been shown herein, the approach to collection of data has worked well and provided both repeatability as well as interesting information suggesting further studies using this technique.

The method developed is applicable to relatively small volumes of fluids and other materials such as greases and so forth. Regarding the particular sequence of break-in load and sequential step loads and step-time intervals, these may be varied according to the intended information desired. This choice also applies to the materials chosen to provide the abrading surfaces. Nonetheless, the modified Falex pin with thermocouple and the vee blocks may be made of the same steel alloy to try to avoid any effect of any significant metallurgical differences between them.

Although the primary focus herein was to evaluate and characterize a test for lubricity as a method, the method may be applied further, for example, in comparing the presumably beneficial effects of using a well-recognized antiwear additive in a simple additive-free base oil. With the two fluids resulting (with and without the additive), the comparative measures sought at progressive increases of load, were 1) failure load, 2) torque, 3) wear, 4) friction-related temperatures, and 5) reproducibility.

The effect shown on failure load was dramatic with an increase of five times the load needed to bring failure. Such response to an additive was a clear statement that the technical approach used in the test for lubricity would be appropriate for the appraisal and comparison of additives. This was shown in the sharp contrast of the base oil failing quickly upon applying the 150-pound load of Step 2, whereas the antiwear-additive-containing base oil was able to tolerate Step 2 to Step 4 for their full 15-minute exposure to each progressive increase in load.

More than this, by the ability to use continuous recording of torque to measure rubbing resistance and to determine wear periodically at the end of each step by measuring the distance between the pincering vee blocks, it was found that, with the particular metals used, even though torque increased to some extent with increasing load, the rate of wear did not change.

As expected, the temperature of the journal was strongly affected by the increasing, pincering load placed by the vee blocks. Following the major temperature increase of break-in, where the journal temperature rose from an ambient 24° C. to about 75° C., the stepped 25-pound increases in vee block load, led to a very uniform 17±1° C. per step increase in the temperature of the journal in both first and second runs, 2 until failure occurred in both at Step 5. Sensitivity and precision of continuously measuring the response of the journal to the wear and friction imposed during testing bespeaks the consistency and information available from this method of measurement.

Over the years of study of wear and lubrication, the various indicators of wear and failure used have provided much information but have been limited in the detail of such studies by their reproducibility. In contrast, by measuring such a closely related property of friction and wear, considerable improvement has been made, particularly when closely approaching failure.

Further Important Considerations

It is important to note that the starting temperatures of the present comparative testing methodology can be varied to obtain additional data with respect to a lubricant. Comparisons, however, between a baseline lubricant or lack thereof, either or both of which may be employed and be considered a type of control, versus a target lubricant, which may be considered to be a candidate lubricant for possible use in the field and/or to be a forensic sample taken from a lubricant used in the field, should be made by employing the same starting temperature(s). A battery of tests may be conducted with starting temperatures based on ambient or otherwise set temperatures at which a target lubricant would be expected to perform in the field. For instance, for a particular target engine oil, test starting temperature(s) of −35° C., −5° C., 20° C., 35° C. and/or 50° C. may be employed, with the same starting temperature(s) used in the corresponding baseline set of lubricant test conditions. Such starting temperatures may delineate or be inclusive of temperatures found during use of machinery in the field, for example, during starting and/or operating of the machinery.

These temperatures (Ts) may be used to determine a ratio (e.g., Ttarget/Tbaseline) for a lubricity index at any given time or all of testing may be used in any suitable temperature scale, for example, degrees Kelvin, degrees Celsius, or degrees Fahrenheit. While the Kelvin scale may be used for lubricity indices of a more absolute nature and/or where readouts would go from negative to positive degrees in other scales, the latter and other scales may magnify results.

Recapitulation

In sum, the importance of understanding the influence and effectiveness of lubricants and additives on correcting wear and extending the life of the mechanisms on which they are used led to the development of the present invention. As often occurs when generating a method of permitting the expression of friction and wear along with an apparatus to carry out the method, the approach taken hereby has shown some unexpected aspects of their relationship and promises further information from future studies.

INCORPORATIONS BY REFERENCE

The aforementioned U.S. provisional patent application No. 62/995,523 plus ASTM D2670-95 (Reapproved 2010) and U.S. Pat. No. 10,302,619 B2, which were incorporated by reference therein by attachment thereto, are incorporated herein by reference in their entireties.

CONCLUSION TO THE INVENTION

The present invention is thus provided. Various feature(s), part(s), step(s), subcombination(s) and/or combination(s) can be employed with or without reference to other feature(s), part(s), step(s), subcombination(s) and/or combination(s) in the practice of the invention, and numerous and sundry adaptations can be effected within its spirit, the literal claim scope of which is particularly pointed out by the following claims:

I claim:

1. A method for obtaining temperature data for measuring lubricity of a sample of a lubricant, which comprises carrying out the following steps (A-G), Which are not required to be carried out in series unless otherwise indicated:
  A. providing a test apparatus having parts that move abrasively in relation to each other, each of the parts that move abrasively in relation to each other having a surface able to be moved in abrasive contact under force with at least one another;
  B. providing a baseline set of lubrication conditions between the surfaces in said contact with one another through addition of a baseline lubricant sample or avoiding employment of an added lubricant between said surfaces in said contact with at least one another;
  C. abrasively moving at least one of said parts and applying force during that abrasive movement such that the abrasively moving forceful contact is carried out between said surfaces under said baseline set of lubrication conditions;
  D. measuring temperature indicative of heat generated during said abrasive movement in abrasive contact under said baseline set of lubrication conditions;
  E. repeating steps A-C, but replacing at least the surfaces of said abrasively movable parts with corresponding, fresh surfaces able to be moved in abrasive contact under force with at least one another, and replacing the baseline set of lubrication conditions with a target set of lubrication conditions through employment of a target lubricant between said surfaces;
  F. measuring temperature generated that is indicative of heat generated during said abrasive movement in abrasive contact under said target set of lubrication conditions; and
  G. comparing the temperatures generated under the baseline and target set of lubrication conditions to generate a lubricity index of the target lubricant sample.

2. The method of claim 1, wherein a thermocouple is provided in at least one of said parts to measure each abrasively generated temperature.

3. The method of claim 1, wherein at least one temperature is measured remotely.

4. The method of claim 1, wherein said added lubricant is avoided in step B.

5. The method of claim 1, wherein the test apparatus is a rotatable pin and vee block test apparatus for ASTM D2760-95 (Reapproved 2010) testing, modified such that its rotatable pin has a central axis with a hole longitudinally along the central axis of the ratable pin about which the ratable pin rotates during testing, with said hole configured to receive and receiving a thermocouple to measure the temperature from heat generated during the testing.

6. The method of claim 5, wherein said baseline lubricant and target lubricant samples are present, and are present as liquids, and the test apparatus does not contain a grease sleeve.

7. The method of claim 6, wherein the liquids are oils.

8. The method of claim 5, wherein said baseline lubricant and target lubricant samples are present, and are present as paste products, and the test apparatus does contain a grease sleeve to contain said baseline lubricant and target lubricant samples.

9. The method of claim 8, wherein the paste products are grease or other organic paste product samples.

10. Test apparatus for obtaining temperature data for measuring lubricity of a liquid lubricant comprising a rotatable pin and we block test apparatus for ASTM D2760-95 (Reapproved 2010) testing, modified such that its rotatable pin has a central axis with, a hole longitudinally along the central axis of the rotatable pin about which the rotatable pin rotates during the testing, with said hole configured to receive a thermocouple to measure the temperature during testing, wherein the following features (I, II) are also present:

I. the test apparatus is such that it is configured to be useful for obtaining the temperature data for measuring the lubricity of a sample of the liquid lubricant, which includes carrying out the following steps (A-G), which are not required to be carried out in series unless otherwise indicated:

A. providing the test apparatus, which has parts that move abrasively in relation to each other, each of the parts that move abrasively in relation to each other having a surface able to be moved in abrasive contact under force with at least one another;

B. providing a baseline set of lubrication conditions between the surfaces in said contact with one another through addition of a baseline lubricant sample of avoiding employment of an added lubricant between said surfaces in said contact with at least one another;

C. abrasively moving at least one of said parts and applying force during that abrasive movement such that the abrasively moving forceful contact is carried out between said surfaces under said baseline set of lubrication conditions;

D. measuring temperature indicative of heat generated during said abrasive movement in abrasive contact under said baseline set of lubrication conditions;

repeating steps A-C, but replacing at least the surfaces of said abrasively movable parts with corresponding, fresh surfaces able to be moved in abrasive contact under force with at least one another, and replacing the baseline set of lubrication conditions with a target set of lubrication conditions through employment of a target lubricant between said surfaces;

F. measuring temperature generated that is indicative of heat generated during said abrasive movement in abrasive contact under said target set of lubrication conditions; and G. comparing the temperatures generated under the baseline and target set of lubrication conditions to generate a lubricity index of the target lubricant sample; and II. the test apparatus does not contain a grease sleeve.

11. The apparatus of claim 10, wherein the thermocouple is received in said hole.

* * * * *